United States Patent
Van Hemelryck et al.

(10) Patent No.: US 12,227,470 B2
(45) Date of Patent: Feb. 18, 2025

(54) PURIFICATION OF ALKYL HYDROPEROXIDE BY EXTRACTIVE DISTILLATION

(71) Applicant: ARKEMA FRANCE, Colombes (FR)

(72) Inventors: Bruno Van Hemelryck, Pierre-Benite (FR); Serge Hub, Pierre-Benite (FR); Philippe Maj, Pierre-Benite (FR)

(73) Assignee: ARKEMA FRANCE, Colombes (FR)

( * ) Notice: Subject to any disclaimer, the term of this patent is extended or adjusted under 35 U.S.C. 154(b) by 599 days.

(21) Appl. No.: 17/417,409

(22) PCT Filed: Dec. 20, 2019

(86) PCT No.: PCT/FR2019/053259
§ 371 (c)(1),
(2) Date: Jun. 23, 2021

(87) PCT Pub. No.: WO2020/136337
PCT Pub. Date: Jul. 2, 2020

(65) Prior Publication Data
US 2022/0073456 A1   Mar. 10, 2022

(30) Foreign Application Priority Data
Dec. 26, 2018   (FR) ...................................... 1874177

(51) Int. Cl.
*C07C 407/00* (2006.01)
*B01D 3/40* (2006.01)

(52) U.S. Cl.
CPC ............ *C07C 407/003* (2013.01); *B01D 3/40* (2013.01)

(58) Field of Classification Search
CPC .................................................. C07C 407/003
See application file for complete search history.

(56) References Cited

U.S. PATENT DOCUMENTS 2,383,919 A * 8/1945 Rust ...................... C07C 407/00
                                                            203/55
4,381,222 A * 4/1983 Brossmann ......... C07C 407/003
                                                            203/92
5,488,177 A * 1/1996 Appel ................. C07C 407/003
                                                            568/576

FOREIGN PATENT DOCUMENTS

CN   107501152 A   12/2017

* cited by examiner

*Primary Examiner* — Rosalynd A Keys
(74) *Attorney, Agent, or Firm* — NK Patent Law

(57) ABSTRACT

The invention relates to a method for purifying an alkyl hydroperoxide from dialkyl peroxide thereof, comprising a step of distillation in the presence of alcohol and water followed by extraction of the condensates using a hydrocarbon or a hydrocarbon blend.

10 Claims, No Drawings

PURIFICATION OF ALKYL HYDROPEROXIDE BY EXTRACTIVE DISTILLATION

CROSS-REFERENCE TO RELATED APPLICATIONS

This application is a U.S. National Stage application of International Patent Application No. PCT/FR2019/053259, filed on Dec. 20, 2019, which claims the benefit of French Patent Application No. 1874177, filed on Dec. 26, 2018.

FIELD OF THE INVENTION

The present invention relates to a process for the separation and purification by means of extractive distillation of organic peroxides, and more particularly the separation of dialkyl peroxides of the general formula $R_1$—OO—$R_2$, with $R_1$ and $R_2$ being identical or non-identical $C_4$ to $C_8$ alkyl structures which may possibly be cyclic.

Thus, more specifically but without being limited to this application, the present invention relates to the purification of alkyl hydroperoxides starting from mixtures containing dialkyl peroxides as defined hereinabove.

This invention finds an application in particular, but not exclusively, in the production of organic peroxides obtained by the synthesis of alkyl hydroperoxides containing dialkyl peroxide impurities. This invention thus makes it possible to obtain, with improved purity, organic peroxides of perester type, such as tert-butyl peroxypivalate, tert-butyl peroxy-2-ethylhexanoate, tert-amyl peroxy-2-ethylhexanoate, of monoperoxypercarbonate type such as OO-tert-butyl-O-(2-ethylhexyl)monoperoxycarbonate, of perketal type such as 2,2-di(tert-butylperoxy)butane, 2,2-di(tert-amylperoxy)butane, of hemiperketal or ether peroxide type, such as 1,1-dimethylpropyl-1-methoxycyclohexyl peroxide and of dialkyl or aryl peroxide type such as 2,5-dimethyl-2,5-di(tert-butylperoxy)hexane peroxide, tert-butyl cumyl peroxide, di(tert-butylperoxyisopropyl)benzene.

The alkyl hydroperoxides are typically tert-amyl hydroperoxide (denoted hereinafter by the abbreviation TAHP) and tert-butyl hydroperoxide (denoted hereinafter by the abbreviation TBHP).

TECHNICAL BACKGROUND

Alkyl hydroperoxides are commonly used as starting materials for producing crosslinkers, intended to be mixed with polymers such as polyester, ethylene-vinyl acetate or ethylene-propylene-diene monomer. They are also used in the production of polymerization initiators, for example initiators of the polymerization of polystyrene or polyethylene.

In general, the alkyl hydroperoxides present on the market contain impurities, mainly represented by dialkyl peroxides, derived from the alkyl hydroperoxides in question. This is because alkyl hydroperoxides are conventionally obtained by acid catalysis, leading to the formation of the associated dialkyl peroxides, which are generally present at between 3% and 30% by weight relative to the total weight of the composition of alkyl hydroperoxides.

These dialkyl peroxides are not desired in combination with their respective alkyl hydroperoxides and represent the main source of harmful/negative contamination in the synthesis of crosslinkers and polymerization initiators.

Thus, these impurities obtained in the alkyl hydroperoxide starting materials enter the process for the production of crosslinkers for polymers and of polymerization initiators. This has the direct consequence of lowering the purity of the products obtained. For certain applications, such as low-density polyethylene obtained by peroxide initiation under very high pressure, the presence of dialkyl peroxide in the initiators can be a source of poor thermal reaction profiles, thus harming the execution of the polymerization.

Research has therefore been carried out for purifying the crosslinkers and the polymerization initiators, in other words for removing these impurities, more particularly in this case dialkyl peroxides. Unfortunately, the results obtained are not satisfactory at present: the purification yields are low, the organic peroxides treated are partially degraded.

It thus appears necessary to find a process which makes it possible to remove these impurities, and particularly the dialkyl peroxides, in the starting materials, i.e. alkyl hydroperoxides, while at the same time preserving the physicochemical properties of the latter.

There are various methods for purification of alkyl hydroperoxides which are well known to the person skilled in the art, for example the washing via the formation of salts which is referred to by the document FR 2455036. Alkyl hydroperoxides are conventionally soluble in water, but their associated dialkyl peroxides are generally much less so. Alkyl hydroperoxides react with a base such as for example sodium hydroxide (NaOH) or potassium hydroxide (KOH), to form a water-soluble alkyl hydroperoxide salt. Thus, by settling, the salt and the water-insoluble organic compounds, including the dialkyl peroxides, are separated. Then, when the use of the alkyl hydroperoxide and not of its salt is required in the later synthesis of the polymerization initiator or of the crosslinker, the alkyl hydroperoxide salt is acidified, for example using an aqueous sulfuric acid solution, in order to reform the alkyl hydroperoxide. The alkyl hydroperoxide is thus recovered by phase separation or by extraction with a solvent, for example a hydrocarbon. The major drawbacks of this technique result on the one hand from its low productivity if it is considered that the same reactor carries out the steps (salt formation/settling, reacidification/extraction), and on the other hand from the formation of saline aqueous effluents. The aqueous effluents formed during the acidification, such as for example potassium sulfate, must be treated. In addition, the use of a base, and of an acid, increases the production costs. Lastly, the dialkyl contents obtained remain too high.

Another purification method is direct distillation, as is described in the document FR 2455036. The distillation of TAHP containing di-tert-amyl peroxide (DTA) is effected in the presence of water under reduced pressure and at a temperature of less than 45° C., making it possible to recover TAHP at the bottom of the column. The distillation makes it possible to obtain a TAHP composition with a residue of 0.8% (8000 ppm) of DTA. These results remain insufficient, in particular for the use of TAHP as starting materials for the production of polymerization initiators. In addition, the TAHP loss is significant, between 4% and 16%, due to a lack of selectivity during the separation of the DTA and/or due to a thermal degradation of the TAHP.

The current solutions existing and proposed for purifying alkyl hydroperoxides of their associated peroxides are insufficient. This is due in particular to the lack of selectivity of the purification treatments, the low yields obtained, and the production costs, but also due to the safety conditions to be taken into account during the purification.

Indeed, it is important to note that the chemical nature of organic peroxides is to decompose thermally, with the formation in particular of flammable vapors.

For reasons of safety and of quality of the product to be purified, it is therefore important to limit the treatment temperature as much as possible, which makes the purification of the organic peroxides all the more difficult.

Therefore, effective solutions are currently being sought in order to obtain a process for the purification of solutions of organic peroxides, more particularly of alkyl hydroperoxides, by removing dialkyl peroxide $R_1$—OO—$R_2$ defined above, without loss or degradation of material, in total safety and with a good yield. There is thus a strong need to obtain purified compositions of organic peroxides which comprise less than 1000 ppm of impurities, indeed even of the order of around one hundred ppm.

SUMMARY OF THE INVENTION

Surprisingly, the applicant has thus discovered that the implementation of a process comprising at least one step a) of distilling a composition comprising the alkyl hydroperoxide and the dialkyl peroxide in the presence of alcohol and water, and at least one step b) of extracting said dialkyl peroxide with the aid of a hydrocarbon makes it possible to selectively remove the dialkyl peroxide from the corresponding alkyl hydroperoxide.

One of the particularly interesting aspects of the present invention resides in the fact that the dialkyl peroxide in the corresponding alkyl hydroperoxide is removed while entraining a reduced amount of this alkyl hydroperoxide in the course of the process according to the invention. The removal of the dialkyl peroxide from the corresponding alkyl hydroperoxide, with a reduced loss of hydroperoxide, is particularly effective when the alcohol introduced into the distillation reboiler is in particular methanol.

The best recovery of dialkyl peroxide combined with the smallest amount of hydroperoxide in the distillation top product is illustrated in particular in the case of the purification of the hydroperoxide TAHP with methanol.

The term "alkyl hydroperoxide" means a compound of the formula R—O—O—H, in which R represents a linear or branched, cyclic or non-cyclic, unsaturated or functionalized alkyl group, or an optionally substituted aromatic group preferably having from 4 to 8 carbon atoms, preferentially from 4 to 6 carbon atoms, more preferentially 4 or 5 carbon atoms.

Preferably, said alkyl hydroperoxide is chosen from the group consisting of tert-butyl hydroperoxide, tert-amyl hydroperoxide, hexylene glycol hydroperoxide, tert-octyl hydroperoxide, tert-hexyl hydroperoxide, 1-methylcyclopentyl hydroperoxide and 1-methylcyclohexyl hydroperoxide. Preferably, the water-soluble organic peroxide is chosen from the group consisting of tert-butyl hydroperoxide and tert-amyl hydroperoxide, more preferentially is tert-amyl hydroperoxide.

The term "dialkyl peroxide" means a compound of the formula $R_1$—O—O—$R_2$, in which $R_1$ and $R_2$ are identical or different and independently represent a linear or branched, cyclic or non-cyclic, unsaturated or functionalized alkyl group, or an optionally substituted aromatic group preferably having from 4 to 8 carbon atoms, preferentially from 5 to 8 carbon atoms, more preferentially from 5 to 7 carbon atoms, or preferentially from 4 to 6 carbon atoms, more preferentially 4 or 5 carbon atoms.

As dialkyl peroxide to be separated from the hydroperoxide, mention may be made of di-tert-butyl peroxide, di-tert-amyl peroxide, di(3-hydroxy-1,1-dimethylbutyl) peroxide, di-tert-octyl peroxide, di-tert-hexyl peroxide, di(methylcyclopentyl) peroxide and di(methylcyclohexyl) peroxide. In particular, the dialkyl peroxide is symmetrical, that is to say that the groups flanking the O—O group are identical.

The characteristics of the water-soluble organic peroxide described in connection with the process for concentration above can be applied in the same manner to the water-soluble organic peroxide in the context of the separation process.

Advantageously, said at least one water-soluble organic peroxide, preferably said at least one hydroperoxide, and said at least one dialkyl peroxide have identical groups R, $R_1$ and $R_2$.

For example, the water-soluble organic peroxide is tert-butyl hydroperoxide and the dialkyl peroxide is di-tert-butyl peroxide.

Alternatively, the water-soluble organic peroxide is tert-amyl hydroperoxide and the dialkyl peroxide is di-tert-amyl peroxide.

Alternatively, the water-soluble organic peroxide is hexylene glycol hydroperoxide and the dialkyl peroxide is di(3-hydroxy-1,1-dimethylbutyl) peroxide.

Alternatively, the water-soluble organic peroxide is tert-octyl hydroperoxide and the dialkyl peroxide is di-tert-octyl peroxide.

Alternatively, the water-soluble organic peroxide is tert-hexyl hydroperoxide and the dialkyl peroxide is di-tert-hexyl peroxide.

Preferably, the alkyl peroxide consists of tert-amyl peroxide (DTA) or tert-butyl peroxide (DI), even more preferentially is tert-amyl peroxide (DTA).

Preferably, the alcohol is chosen from the group consisting of methanol, tert-amyl alcohol and ethanol. Preferentially, the alcohol is chosen from the group consisting of methanol, tert-amyl alcohol and ethanol. Even more preferentially, the alcohol is methanol.

Other characteristics of this purification process are presented hereinbelow:
preferably, the content by weight of alcohol present in the distillation step a) is greater than 5 times, preferably is greater than 10 times, preferably is greater than 25 times and more preferentially is greater than 30 times that of said dialkyl peroxide,
preferably, the extraction step b) is performed by contacting said hydrocarbon with the condensate obtained in step a) so as to obtain an organic phase containing said hydrocarbon and also all or some of the dialkyl peroxide and an aqueous phase containing the hydroperoxide, the water and the alcohol,
alternatively, the hydrocarbon can be present in the composition before the distillation step a), or introduced in the course of the distillation step;
advantageously, the steps a) and b) can be performed concomitantly;
advantageously, following the step of evaporation of the alcoholic composition, the latter undergoes a step of condensation and then passage into at least one hydrocarbon, so as to obtain an organic phase containing said hydrocarbon and also all or some of the dialkyl peroxide $R_1$—OO—$R_2$ and an aqueous phase containing the water and the alcohol; in other words, step a) can comprise a step of condensation, subsequent to the distillation step;
very advantageously, the hydrocarbon is chosen from $C_6$ to $C_{12}$ hydrocarbons, preferably $C_6$ to $C_8$ hydrocarbons, more preferentially a $C_7$ hydrocarbon;
preferably, the hydrocarbon is saturated;
advantageously, the abovementioned aqueous alcoholic phase, i.e. the aqueous phase obtained in step a), is recycled to the reboiler of the distillation so as to in particular conserve the amount of alcohol required to maintain the purification;

according to one possibility offered by the invention, the abovementioned organic phase is distilled in order to separate said hydrocarbon from the dialkyl peroxide;

advantageously, the distillation of the mixture according to the invention (alkyl hydroperoxide R—OOH/alcohol/dialkyl peroxide R—OO—R/water) is performed at a temperature of between 25° C. and 60° C., preferentially between 30° C. and 45° C.;

advantageously, the distillation of the mixture according to the invention (alkyl hydroperoxide R—OOH/alcohol/dialkyl peroxide $R_1$—O—O—$R_2$/water) is performed at a pressure of between 30 and 200 mbar (millibars), preferentially between 40 and 180 mbar, and more preferentially between 50 and 160 mbar;

more advantageously, the distillation of the mixture according to the invention (alkyl hydroperoxide R—OOH/alcohol/dialkyl peroxide $R_1$—O—O—$R_2$/water) is performed at a pressure of between 90 and 200 mbar (millibars), preferentially between 100 and 180 mbar, and more preferentially between 100 and 160 mbar.

The applicant has thus discovered a selective and secure extractive distillation process avoiding the loss and/or the thermal degradation of the organic peroxides. Said process comprises a distillation step which is more selective in dialkyl peroxide, and also, very advantageously, the recovery thereof by selective extraction in a hydrocarbon.

This offers both the advantage of reducing the heating of the peroxide mixture in total safety and the advantage of easily recycling the solvents water and alcohol which have contributed to the purification.

The use of a composition comprising an alcohol makes it possible to remove the dialkyl peroxide in the hydroperoxide to be purified while generating a dilute solution of alkyl hydroperoxide with alcohol and water, which can be easily removed by direct distillation and then by settling, these being known to the person skilled in the art.

Advantageously, the alcohol used is methanol since it makes it possible to obtain a better recovery of dialkyl peroxide combined with a smaller amount of hydroperoxide in the distillation top product.

The following description is given solely by way of nonlimiting illustration.

DETAILED DESCRIPTION OF THE INVENTION

Distillation, evaporation and extraction are methods well known per se to the person skilled in the art.

The condensation of the distillation top product comprising the dialkyl peroxide to be removed, that is to say the condensation step, preferentially takes place between −30° C. and 0° C., preferentially between −20° C. and −10° C. The distillation top product is recovered by any means well known to the person skilled in the art, such as for example a condenser.

During the passage of the composition comprising the dialkyl peroxide to be removed into a hydrocarbon, the hydrocarbon is maintained in liquid form by adjustment of the temperature, this preferentially being between −30° C. and 0° C., very preferentially between −20° C. and −10° C., in order to limit the risk of boiling of the alcohol phase and to maintain good separation of the phases during the selective capturing of the dialkyl peroxide by the hydrocarbon.

The hydrocarbon is preferably chosen from hydrocarbons comprising from 6 to 12 carbon atoms. Said hydrocarbons comprising from 6 to 12 carbon atoms remain liquid at the condensation temperature of the distillation top product. $C_7$ hydrocarbons are preferred for their ease of removal in the event of entrainment with the alcoholic solution into the reboiler during its recycling.

On contact of the top composition with the hydrocarbon, two phases form, an upper organic phase consisting of the dialkyl peroxide and the hydrocarbon and a lower aqueous phase comprising the mixture of water and alcohol.

Advantageously, the choice of hydrocarbon allows for selective retention of the dialkyl peroxide such as DTA or DI.

The aqueous phase can thus be recycled into the mixture to be purified so as to enable the depletion of dialkyl peroxide by means of distillation. The recycling can be done continuously or batchwise.

The purification process according to the invention, that is to say including the evaporation of the alcoholic composition, its condensation, its extraction by the hydrocarbon and the recycling of the aqueous phase generated, can be performed batchwise, semi-continuously or continuously, depending on the manner in which the peroxide to be purified, the alcohol, the water and the hydrocarbon are supplied.

During the distillation, the hydrocarbon becomes concentrated in dialkyl peroxide. This hydrocarbon solution can be withdrawn and renewed continuously. This hydrocarbon solution comprising the dialkyl peroxide can be distilled so as to recycle the hydrocarbon to the purification process according to the invention, and to profitably exploit the dialkyl peroxide thus isolated.

At the end of the batch distillation according to the invention, the purified mixture generally comprises the alkyl hydroperoxide, water and alcohol. A major amount of water and alcohol can be removed by any means well known to the person skilled in the art, for example by evaporation, for example by heating the mixture to a temperature of between 3° and 50° C., under reduced pressure of between 60 and 200 mbar.

During the distillation process, the degradation of the alkyl hydroperoxide is between 0% and 1% by weight relative to the organic peroxide initially present in the solution to be purified.

The separation process according to the invention can comprise a step a'), prior to step a), of synthesizing said alkyl hydroperoxide.

Step a') of synthesizing the alkyl hydroperoxide can be effected by any method known to the person skilled in the art which leads to the formation of dialkyl peroxide as an impurity. In particular, step a') can be performed via the reaction of at least one alcohol or at least one alkene with hydrogen peroxide in the presence of an acid, preferably sulfuric acid. Such a process results in particular in the synthesis of dialkyl peroxide as impurities.

Preferably, the alkyl hydroperoxide can be prepared in an acidic medium.

In this case, synthesis step a') consists in particular in reacting oxygenated water (hydrogen peroxide) in the presence of at least one alcohol or at least one alkene in an acidic medium.

Preferably, synthesis step a') consists in particular in reacting oxygenated water (hydrogen peroxide) in the presence of at least one alcohol or an unsaturated compound in an acidic medium.

Synthesis step a') may be effected at a temperature which can range from 10° C. to 80° C., preferably from 20° C. to 40° C.

Preferably, synthesis step a') is effected in the presence of one or more inorganic or organic acids, in particular one or more inorganic acids.

More preferentially, the inorganic acid is sulfuric acid.

The composition comprising at least one alkyl hydroperoxide and at least one dialkyl peroxide (before step a)) can comprise at least 50% by weight of alkyl hydroperoxide, preferably at least 60% by weight of alkyl hydroperoxide, more preferentially at least 68% by weight of alkyl hydroperoxide, even more preferentially at least 70% by weight of alkyl hydroperoxide, relative to the total weight of organic peroxides.

According to some embodiments, the composition comprising an alkyl hydroperoxide and a dialkyl peroxide (before step a)) comprises from 0.1% to 40% by weight of dialkyl peroxide, preferably from 1% to 30% by weight of dialkyl peroxide, more preferentially from 2% to 22% by weight of dialkyl peroxide, even more preferentially from 3% to 20% by weight of dialkyl peroxide, relative to the total weight of alkyl hydroperoxide and dialkyl peroxide.

The present invention also relates to a composition of alkyl hydroperoxide obtainable by the process according to the invention.

Preferably, the composition thus obtained comprises less than 1% by weight of alcohol, preferably less than 1000 ppm, and even more preferably less than 100 ppm, relative to the total weight of the composition.

Advantageously, the composition thus obtained comprises less than 1000 ppm of hydrocarbon relative to the total weight of said composition, preferably less than 100 ppm.

Another subject of the present invention relates to a purified composition of alkyl hydroperoxide comprising less than 1000 ppm of dialkyl peroxide, preferentially less than 500 ppm, preferentially less than 250 ppm, and more preferentially less than 100 ppm of dialkyl peroxide.

Preferably, said composition is an aqueous composition containing at least 60% by weight of alkyl hydroperoxide, as defined above, and less than 1000 ppm by weight of dialkyl peroxide as defined above, the proportions being calculated by weight relative to the total weight of the composition.

Preferably, the aqueous composition contains at least 70% by weight of alkyl hydroperoxide, as defined above, more preferentially at least 80% by weight.

Preferably, the group R of the alkyl hydroperoxide as defined hereinabove represents a branched, optionally substituted $C_4$-$C_5$, preferably $C_5$-$C_5$, more preferentially $C_5$-$C_6$, even more preferably $C_5$, alkyl group.

The alkyl hydroperoxide is preferably chosen from the group consisting of tert-amyl hydroperoxide, hexylene glycol hydroperoxide, tert-octyl hydroperoxide and tert-hexyl hydroperoxide.

More preferentially, the alkyl hydroperoxide is tert-amyl hydroperoxide (TAHP).

Advantageously, the aqueous composition contains less than 800 ppm by weight, preferably less than 700 ppm by weight of dialkyl peroxide, preferably less than 500 ppm by weight of dialkyl peroxide, preferably less than 250 ppm by weight of dialkyl peroxide, more preferentially less than 100 ppm by weight of dialkyl peroxide, relative to the total weight of the composition.

Preferably, the dialkyl peroxide chosen from the group consisting of di-tert-amyl peroxide, di(3-hydroxy-1,1-dimethylbutyl) peroxide, di-tert-octyl peroxide and di-tert-hexyl peroxide.

More preferentially, the dialkyl peroxide is di-tert-amyl peroxide.

Advantageously, the composition is a composition of tert-amyl hydroperoxide and comprises less than 1000 ppm of dialkyl peroxide, preferentially less than 1000 ppm of tert-amyl peroxide (DTA).

Advantageously, the aqueous composition contains at least 60% by weight of tert-amyl hydroperoxide (TAHP) and less than 1000 ppm by weight of di-tert-amyl peroxide (DTA), the proportions being calculated by weight relative to the total weight of the composition.

The present invention also relates to the use of the composition as defined above for the preparation of crosslinking agent(s) or polymerization initiator(s).

Preferably, the initiator(s) is or are initiators of freeradical polymerization, in particular of ethylene under high pressure.

For the purposes of the present invention, "high pressure" means a pressure greater than 50 MPa. Preferably, the pressure varies from 500 bar (50 MPa) to 3000 bar (300 MPa), preferentially from 1200 bar (120 MPa) to 3000 bar (300 MPa), better still from 1200 bar (120 MPa) to 2600 bar (260 MPa).

Preferably, the crosslinking agents or the polymerization initiators are chosen from the group consisting of organic peroxides, in particular peroxyesters, hemiperoxyacetals and peroxyacetals.

The term "hemiperoxyacetal" means a compound of the general formula $(R_3)(R_4)C(—OR_1)(—OOR_2)$, in which:
- $R_1$ represents a linear or branched, preferably $C_1$-$C_{12}$, preferably $C_1$-$C_4$, more preferably $C_1$, alkyl group, or a cycloalkyl group with $R_2$,
- $R_2$ represents a linear or branched, preferably $C_1$-$C_{12}$, preferably $C_4$-$C_{12}$, more preferably $C_5$, alkyl group, or a cycloalkyl group with $R_1$,
- $R_3$ represents a hydrogen atom or a linear or branched, preferably $C_1$-$C_{12}$, more preferably $C_4$-$C_{12}$, alkyl group, or a cycloalkyl group with $R_4$,
- $R_4$ represents a hydrogen atom or a linear or branched, preferably $C_1$-$C_{12}$, more preferably $C_4$-$C_{12}$, alkyl group, or a cycloalkyl group with $R_3$.

Preferably, $R_3$ forms a cycloalkyl group with $R_4$.

Preferably, when $R_3$ is a hydrogen atom, $R_4$ is a linear or branched, preferably $C_1$-$C_{12}$, more preferably $C_4$-$C_{12}$, alkyl group.

In the description of the present invention, the percentages are indicated by weight; "ppm" signifies parts per million by weight.

The examples that follow illustrate the invention without limiting it.

EXAMPLES

Example 1: Purification by Extractive Distillation of a Solution of TAHP

Set-Up:

The set-up consists of a flask surmounted by a distillation column equipped with temperature measurement means at the bottom and at the top. A condenser is attached at the top of the column to condense the vapors.

The system for recovering/separating the overhead vapors (Dean-Stark type) is connected to the condenser and has a cooled jacket. This system contains the hydrocarbon which makes it possible to recover the DTA and the methanolic aqueous phase.

This system is equipped with a bottom valve which makes it possible to recycle the lower methanolic aqueous phase to the reboiler of the column.

The reboiler is stirred and heated. The distillation is carried out under a vacuum of approximately 110 mbar. At equilibrium, the temperature of the reboiler is approximately 31° C. and at the top of the column is approximately 28° C.

The vapors condense in the condenser and the condensate falls into the hydrocarbon. On contact with the hydrocarbon, two phases form. The DTA is selectively retained in the upper organic phase and the methanol forms with the water the lower methanolic aqueous phase which is recycled to the reboiler.

The distillation is continued by proceeding in the manner described until virtually all of the DTA is removed from the reboiler.

Starting Mixture:

The mixture to be distilled is produced by mixing commercial TAHP, comprising DTA, with methanol and water so as to obtain the following composition of: 58.7 g of TAHP, 3.1 g of DTA, 74.5 g of methanol and 79.8 g of water.

Into the (Dean-Stark) recovery/separation system are introduced 2.1 g of water, 3.9 g of methanol and 15.7 g of isododecane hydrocarbon.

At the end of extractive distillation, 200.8 g of solution containing 0.02 g of DTA, 57.5 g of TAHP and 65.6 g of methanol are recovered in the reboiler.

18.5 g of hydrocarbon phase containing 3 g of DTA and 15.5 g of hydrocarbon are recovered in the distillation top product.

After the removal of the DTA, the contents of the reboiler are distilled to remove the methanol in the same experimental system. The procedure is similar to the preceding one, except that nothing is recycled to the reboiler during this second distillation. Thus, 102.0 g of the previous mixture (composed of 28.3 g of TAHP, 33.8 g of MeOH and 39.9 g of water) are introduced into the reboiler. The distillation is then performed with a bath temperature of 32 to 35° C. and a partial vacuum of from 120 to 80 mbar. After distillation, the solution in the reboiler separates into 2 phases, the upper organic phase (27.6 g) is composed of 23.3 g of TAHP, 0.25 g of methanol and 4 g of water. DTA is no longer detected by gas-phase chromatography within the detection limit of <100 ppm. The lower aqueous phase (27.2 g) is composed of 1.5 g of TAHP, 0.4 g of methanol and 25.3 g of water. At the top of the column, 3.2 g of TAHP are recovered with the condensed methanol.

This example shows the possibility of reducing the amount of DTA present in the commercial TAHP to a content of around one hundred ppm (0.01%), by virtue of the extractive distillation according to the invention, and in total safety.

Example 2

Example 2a: Extractive Distillation of TAHP Using Alcohols Other than Methanol

Extractive distillation as described in example 1 was performed with alcohols other than methanol, such as tert-amyl alcohol and ethanol. The distillation of these mixtures was performed under total reflux for around one hundred minutes at 40° C. The DTA/alcohol/water mixtures subjected to distillation were mixed in a 1:1:1 weight ratio.

The products obtained in the distillation top product are presented below.

TABLE 1

| Alcohol | TAHP % | DTA % | Alcohol % | P (mbar) at 40° C. |
|---|---|---|---|---|
| Methanol | 1.1 | 8.3 | 75.1 | 150 |
| Tert-amyl alcohol | 3.1 | 4.6 | 57.9 | 74 |
| Ethanol | 3.1 | 6.8 | 60.1 | 93 |

These experiments show that the process according to the invention, comprising a step of distillation in the presence of water and of the alcohols mentioned above, makes it possible to obtain a high entrainment rate of DTA to be removed.

These experiments also show that methanol is particularly advantageous for leading to a high entrainment rate of DTA to be removed, while at the same time minimizing the entrainment rate of TAHP in the distillation top product.

Example 3: Removal of Di-Tert-Butyl Peroxide (DI) in Tert-Butyl Hydroperoxide (TBH)

The set-up created corresponds to the set-up of example 1. The starting mixture is composed of 34.7 g of tert-butyl hydroperoxide (TBH), 2.7 g of di-tert-butyl peroxide (DI), 49.4 g of methanol and 62.4 g of water. This mixture is placed in the flask at the distillation bottom.

The Dean-Stark apparatus is initially charged with a methanolic aqueous phase composed of 2.4 g of water, 1.7 g of methanol, and an upper phase of 6.9 g of isododecane. The amount of DI present in the distillation bottom in the initial TBH thus diluted is 1.8% by weight of the methanolic composition.

The flask is heated with the aid of a water bath, set to 35° C., and is stirred with a magnetic bar at 500 rpm. The distillation is performed under a vacuum of between 112 mbar (millibar) and 106 mbar, in order to maintain a top temperature of between 28° C. and 30° C. The condensates are recovered in the Dean-Stark apparatus containing the isododecane. Thus, 2 phases appear, the upper hydrocarbon phase containing the DI and a lower water-methanol phase. The latter is recycled to the bottom. The method makes it possible to reduce the amount of DI to 0.17% by weight of the bottom composition by the selective removal permitted by the capture of the DI in the hydrocarbon, according to the invention. If the distillation is continued further, the amount of DI is lowered further to 0.07% in the bottom composition.

Example 4: Simple Distillation of the Mixture as in Example 3 without Hydrocarbon in the Dean-Stark Apparatus A mixture comprising TBH, DI, MeOH and water, of the following weight composition: DI/methanol/water/TBH 3.5%/32.6%/64.0%/27.9% respectively, was distilled but without hydrocarbon in the Dean-Stark apparatus. The condensed vapors were not recycled to the reboiler. GC analysis of the distillation top product at equilibrium indicates a DI/MeOH/water/TBH composition of 48.2%/36.5%/10.7%/4.6% (top temperature of between 30.4° C. and 31° C. and a pressure of between 115 mbar and 119 mbar). After 180 minutes, the analysis of the distillation bottom indicates a depletion of DI, but not as significantly as in example 3 since it still represents 2.1% for 28.9% of TBHP and 31.6% of methanol. This experiment shows that in the absence of recovery of the DI by extraction with hydrocarbon, the recycling of methanol to the bottom is not possible and the distillation is no longer as efficient.

The invention claimed is:

1. A process for separating an alkyl hydroperoxide from a dialkyl peroxide, comprising the steps of: a) distilling a composition comprising the alkyl hydroperoxide and said dialkyl peroxide in the presence of alcohol and water, and b) extracting the dialkyl peroxide with the aid of a hydrocarbon, wherein the extraction step b) is performed by contacting said hydrocarbon with the condensate obtained in step a) so as to obtain an organic phase containing said hydrocarbon and also all or some of the dialkyl peroxide and an aqueous phase containing the hydroperoxide, the water and the alcohol.

2. The process as claimed in claim 1, wherein the alkyl hydroperoxide is selected from the group consisting of tert-butyl hydroperoxide, tert-amyl hydroperoxide, hexylene glycol hydroperoxide, tert-octyl hydroperoxide, tert-hexyl hydroperoxide, 1-methylcyclopentyl hydroperoxide and 1-methylcyclohexyl hydroperoxide.

3. The process as claimed in claim 1, wherein the dialkyl peroxide is selected from the group consisting of di-tert-butyl peroxide, di-tert-amyl peroxide, di(3-hydroxy-1,1-dimethylbutyl) peroxide, di-tert-octyl peroxide, di-tert-hexyl peroxide, di(1-methylcyclopentyl) peroxide and di(1-methylcyclohexyl) peroxide.

4. The process as claimed in claim 1, wherein the content by weight of alcohol present in step a) is greater than 5 times that of said dialkyl peroxide.

5. The process as claimed in claim 1, wherein the hydrocarbon is selected from the group consisting of $C_6$ to $C_{12}$ hydrocarbons.

6. The process as claimed in claim 1, wherein the aqueous phase obtained in step a) is recycled to the reboiler of the distillation.

7. The process as claimed in claim 1, wherein the contacting said hydrocarbon with the condensate obtained in step a) takes place in a condenser and the organic phase from the condenser is distilled in order to separate the hydrocarbon(s) from the dialkyl peroxide.

8. The process as claimed in claim 1, wherein the distillation step a) is carried out at a temperature of between 25° C. and 60° C.

9. The process as claimed in claim 1, wherein the distillation step a) is carried out at a pressure of between 30 and 200 mbar (millibars).

10. The process as claimed in claim 1, wherein it comprises a step a'), prior to step a), of synthesizing said alkyl hydroperoxide in an acidic medium.

* * * * *